United States Patent [19]

Elson

[11] Patent Number: 5,346,476
[45] Date of Patent: Sep. 13, 1994

[54] FLUID DELIVERY SYSTEM

[75] Inventor: Edward E. Elson, 4356 Claytor Cir., Anaheim, Calif. 92806

[73] Assignee: Edward E. Elson, Anaheim, Calif.

[21] Appl. No.: 875,756

[22] Filed: Apr. 29, 1992

[51] Int. Cl.$^5$ .......................... A61M 5/20; A61M 5/00
[52] U.S. Cl. ..................................... 604/135; 604/246
[58] Field of Search .............. 604/132, 134, 135, 143, 604/246, 249, 250; 222/92, 95, 105, 633, 386, 211, 386.5; 128/DIG. 12

[56] References Cited

U.S. PATENT DOCUMENTS

| | | |
|---|---|---|
| 2,816,690 | 12/1957 | Lari . |
| 3,361,303 | 1/1968 | Jacuzzi . |
| 3,412,906 | 11/1968 | Dinger . |
| 3,468,308 | 9/1969 | Bierman . |
| 3,469,578 | 9/1969 | Bierman . |
| 3,486,539 | 12/1969 | Jacuzzi . |
| 3,506,005 | 4/1970 | Gilio et al. . |
| 3,565,292 | 2/1971 | Jinotti . |
| 3,672,543 | 6/1972 | Roper et al. . |
| 3,677,444 | 8/1972 | Merrill . |
| 3,698,595 | 10/1972 | Gortz et al. . |
| 3,734,351 | 5/1973 | Gaudin . |
| 3,738,538 | 6/1973 | Roper et al. . |
| 3,767,078 | 10/1973 | Gortz et al. . |
| 3,780,732 | 12/1973 | Leibinsoh . |
| 3,791,557 | 2/1974 | Venus . |
| 3,796,356 | 3/1974 | Venus . |
| 3,809,087 | 5/1974 | Lewis, Jr. ............... 604/134 |
| 3,876,115 | 4/1975 | Venus . |
| 3,895,741 | 7/1975 | Nugent . |
| 3,907,169 | 9/1975 | Gortz et al. . |
| 3,940,026 | 2/1976 | Kain . |
| 3,961,725 | 6/1976 | Clark . |
| 3,981,415 | 9/1976 | Fowler et al. . |
| 4,140,117 | 2/1979 | Buckles et al. . |
| 4,222,499 | 9/1980 | Lee et al. . |
| 4,318,400 | 3/1982 | Peery et al. . |
| 4,324,242 | 4/1982 | Cross . |
| 4,324,350 | 4/1982 | Thompson . |
| 4,337,769 | 7/1982 | Olson . |
| 4,386,929 | 6/1983 | Peery et al. . |
| 4,419,096 | 12/1983 | Leeper et al. . |
| 4,430,078 | 2/1984 | Sprague . |
| 4,446,991 | 5/1984 | Thompson . |
| 4,458,830 | 7/1984 | Werding . |
| 4,491,247 | 1/1985 | Nitchman et al. . |
| 4,500,308 | 2/1985 | Kurtz et al. ............... 604/135 X |
| 4,504,267 | 3/1985 | Parmelee et al. . |
| 4,561,856 | 12/1985 | Cochran ............... 604/143 |
| 4,564,127 | 1/1986 | Garabedian et al. . |
| 4,645,486 | 2/1987 | Beal et al. . |
| 4,702,397 | 10/1987 | Gortz . |
| 4,718,893 | 1/1988 | Dorman et al. ............... 604/134 X |
| 4,769,008 | 9/1988 | Hessel . |
| 4,867,743 | 9/1989 | Vaillancourt ............... 604/135 |
| 4,874,386 | 10/1989 | O $\propto$ Boyle ............... 604/135 X |
| 4,938,751 | 7/1990 | Leeper et al. ............... 604/132 |
| 4,953,753 | 9/1990 | Gortz . |
| 4,991,742 | 2/1991 | Chang ............... 604/135 X |
| 4,997,420 | 3/1991 | LeFevre ............... 604/135 X |
| 5,100,389 | 3/1992 | Vaillancourt . |

Primary Examiner—Randall L. Green
Assistant Examiner—Elizabeth M. Burke
Attorney, Agent, or Firm—Michael J. Ram

[57] ABSTRACT

Disclosed is a fluid delivery system comprising a bladder to hold a fluid, the bladder being enclosed in a structure formed from a cap connected to a drive mechanism. The drive mechanism includes a piston driven by a constant force spring, the piston resting against the bladder. Activation of the drive mechanism delivers the fluid at a rate pre-determined by the design of the spring.

17 Claims, 6 Drawing Sheets

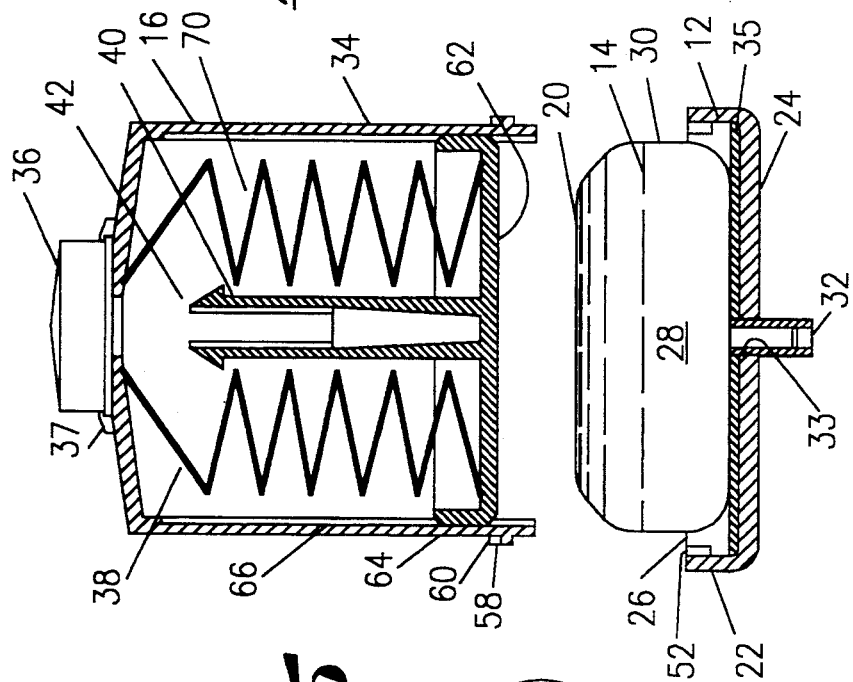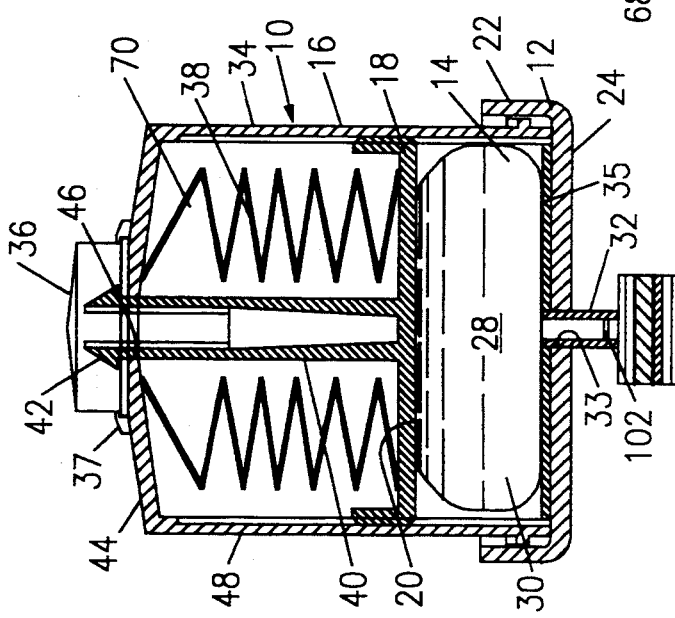

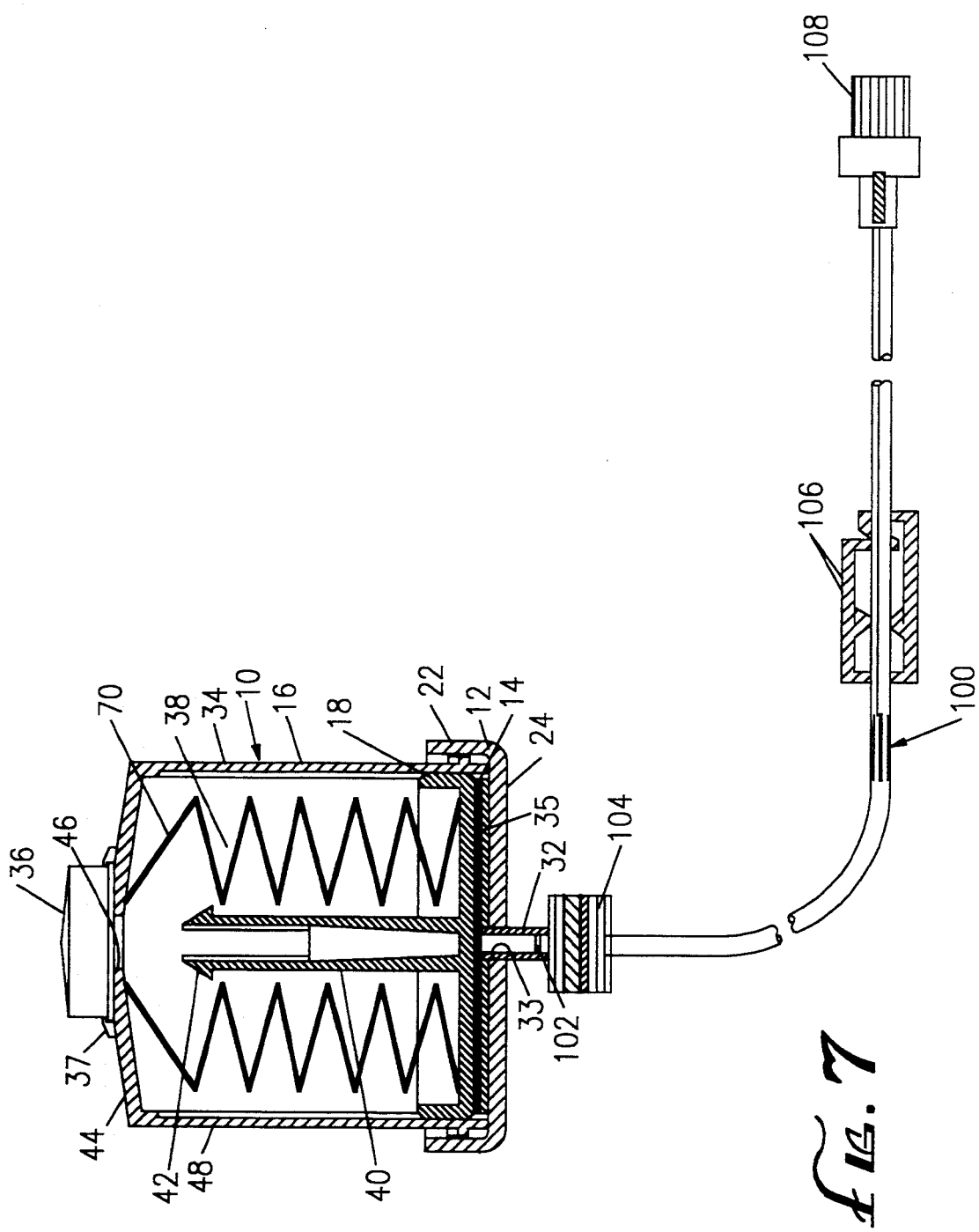

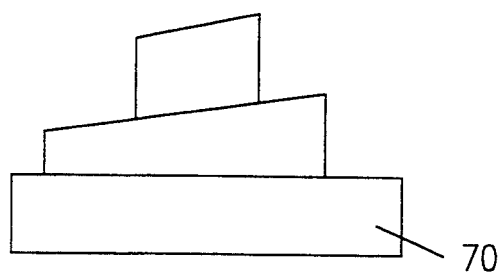
*fig.*11A
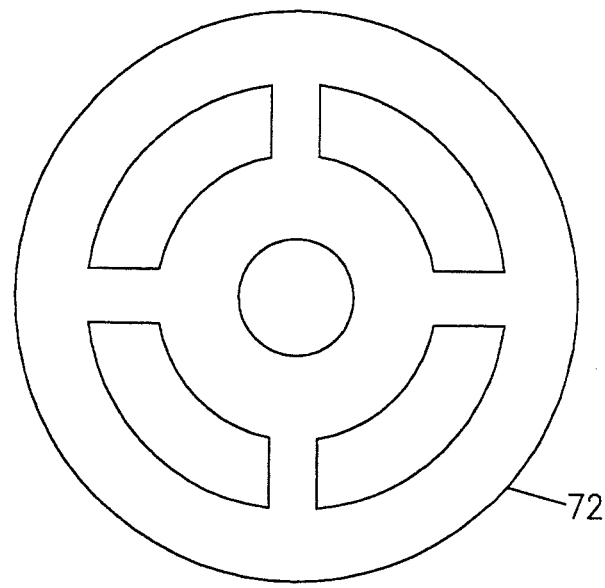
*fig.*12B
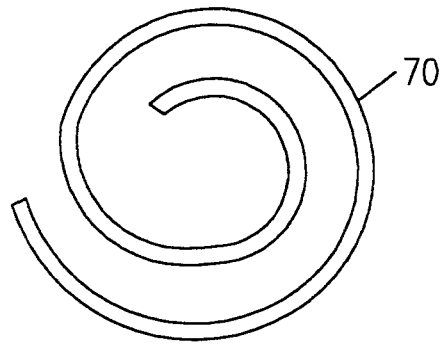
*fig.*11B
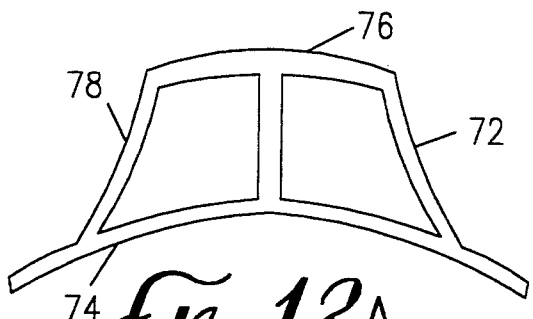
*fig.*12A
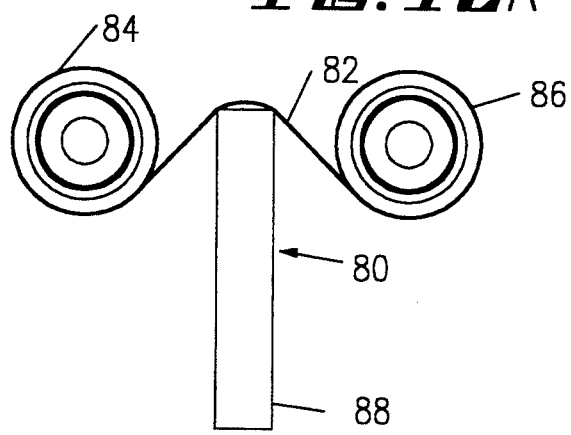
*fig.*13

FLUID DELIVERY SYSTEM

BACKGROUND

The present invention relates to delivery systems for fluids. In particular, the invention is directed to a easily assembled and portable system for infusion of fluids such as intravenous solutions, blood plasma or drug solutions at a controlled delivery rate.

Various devices and methods are known for delivery of fluids to a patient. The simplest method utilizes gravity feed from a bag or bottle filled with the fluid suspended above the patient, possibly with a flow restrictor or drip chamber in the tubing connecting the bag to the patient. However, the flow rate can vary depending on many variables such as the height of the fluid bag above the patient, the content of the bag or the tubing or needle size. Also, it is sometimes desirable to deliver the fluids at an accelerated rate or at controlled but nonconstant rate. This can not be readily managed by a gravity feed system.

One of the more complicated methods is to utilize a motor driven pump which is computer controlled and thus is capable of being programmed to deliver fluid at very precise rates. While such devices may be useful at the bed side in a stationary position they are expensive and easily damaged and thus are not preferred for ambulatory use.

Previous attempts to produce a portable device which is resistant to damage and tampering has resulted in expensive and cumbersome products which are not readily controllable. Examples of such devices include inflatable cuffs, pressurized bladders and spring loaded clamps or platforms. However, these devices generally do not offer means for controlling flow.

Thus, there is a need for a simple, portable fluid delivery system which also allows medical personnel to readily control delivery rates of the fluids to the patient.

SUMMARY

These needs are met by the present invention which comprises a fluid delivery system having a bladder carried within a cap and a drive mechanism attached to the cap and mounted over the bladder. In a preferred embodiment, the drive mechanism comprises a piston which rests on the bladder and a spring which forces the piston against the bladder expelling the fluid from the bladder at a controlled rate. The delivery rate is controlled by varying the manner of construction, materials, cross section, thickness, and other parameters of the spring.

Further embodiments of the present invention include a fluid delivery system in combination with tubing sets for delivery of the fluid to the patient. The tubing set can include flow restriction devices which act in cooperation with the drive mechanism to further control the flow of fluid.

DRAWINGS

These and other features, aspects and advantages of the present invention will become better understood with reference to the following description, appended claims, and accompanying drawings, where:

FIG. 4 is a cutaway expanded side view of the fluid delivery system of FIG. 1 with the piston in its unloaded position, the cut away view taken along line 3—3 of FIG. 1.

FIG. 5 is a cut away side view of the fully assembled fluid delivery system of FIG. 1 with addition of a tubing set, the cut away view taken along line 1—1 of FIG. 1.

FIG. 6 is a bottom view of the knob portion of the fluid delivery system of FIG. 1.

FIG. 7 is a cut away side view of the fluid delivery system and delivery tube of FIG. 5 with the bladder empty, the cut away view taken along line 3—3 of FIG. 1.

FIGS. 11a, 12a, 11b and 12b are side views and top views, respectively, of a spiral spring design and a dome spring design for use in the fluid delivery system of FIG. 1 or FIG. 8.

FIG. 13 shows a drive system based on the negator spring concept.

DESCRIPTION

Figure 1:
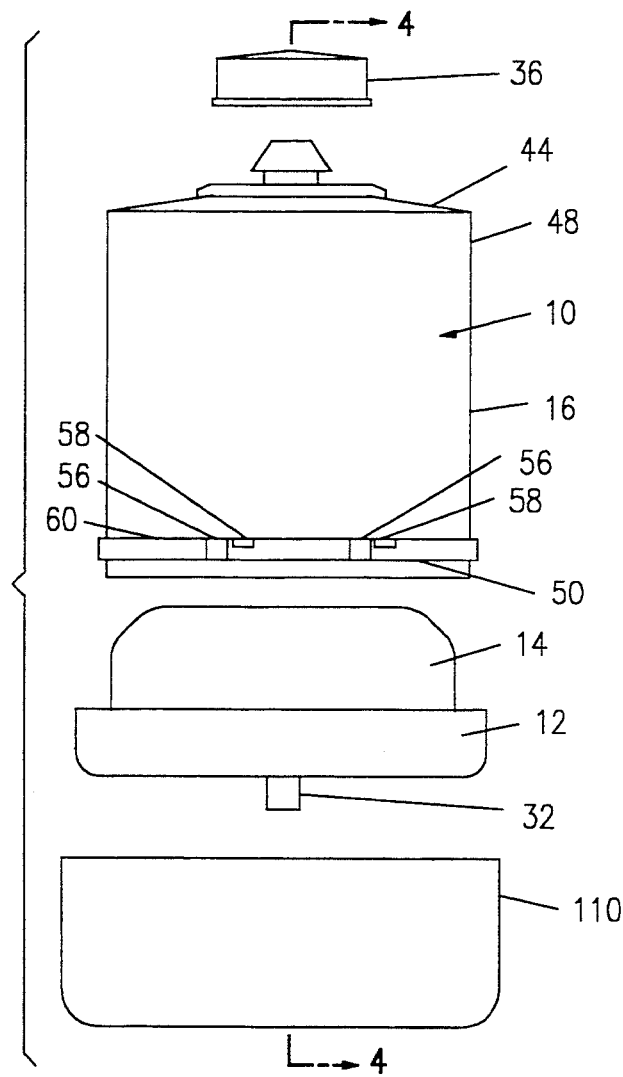
FIG. 1 is an exploded side view of a first embodiment of the fluid delivery system.

FIGS. 1 through 7 show a first embodiment of a fluid delivery system 10 embodying features of the invention.

The fluid delivery system 10 comprises a cap 12, a removable bladder 14 carried within the cap 12 and a drive mechanism 16 attached to the cap 12. A piston 18 is enclosed within the drive mechanism 16 in contact with the upper surface 20 of the bladder 14.

The cap 12 has a cylindrical wall 22, a closed end 24 and an open end 26.

The bladder 14 located inside the cap 12 contains the fluid 28 to be delivered. The bladder 14 has at least one access port in the wall 30 of the bladder 14 to allow removal of fluid 28 from the bladder 14. The access port may also be used to fill the bladder or a second filling means may be made available for this purpose. The access port is accessible through the cap 12 when the fluid delivery system 10 is assembled. In, the embodiment in the figures the access port is a tubing connector 32, which may also include a valve (not shown), which extends through an opening 33 in the closed end 24 of the cap. Preferentially, a one way valve is used to prevent retrograde flow. Alternate access or filling means include a septum which can be pierced by a needle or a spike or a tube with an external clamp. Other suitable access means standard in the art and connectors such as threaded, bayonet or luer lock connectors are also usable.

Figure 10:
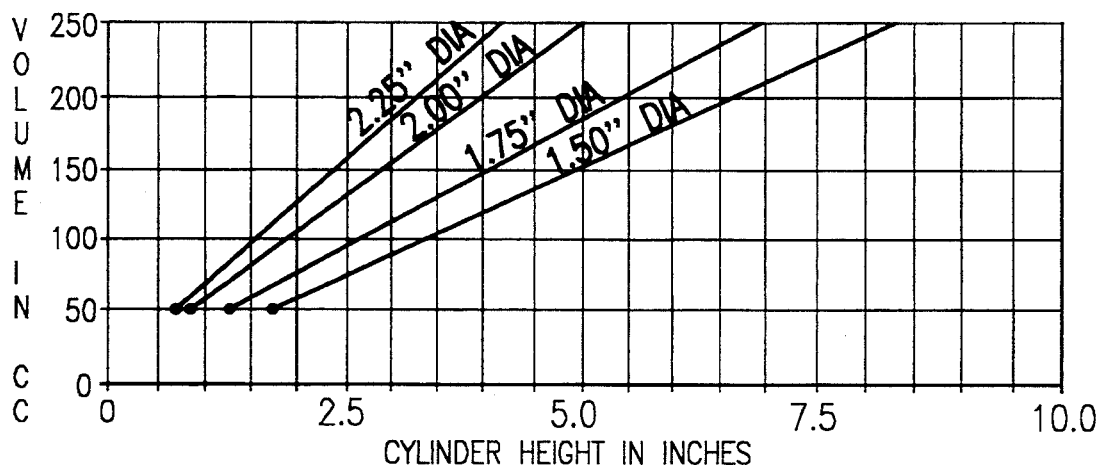
FIG. 10 is a graph showing the filled volume of bladders having different dimensions.

The bladder 14 can be chosen to have a capacity appropriate for the amount of fluid to be delivered and the time period for fluid delivery. FIG. 10 is a graph showing how the capacity of a cylindrical bladder varies with the height and diameter of the bladder. Other three-dimensional shapes, such as spherical or square bladders can also be used to expand or limit the quantity of fluid delivered with a fixed rate drive mechanism.

The drive mechanism 16 comprises a shell 34, a piston 36 which is free to move within the shell 34, a pressure means which forces the piston 18 against the upper surface 20 of the bladder 14 and a knob 36 on the top of the shell to retain the pressure means in a loaded position until released by the operator. The knob 36 is held on the shell 34 by a collar 37 integral with the shell 34, the collar surrounding the hole 46. A preferred pressure means is a specially designed spring 38, which is described below. The piston 18 shown in the drawings includes an upwardly extending shaft 40 with a barbed upper end 42, the shaft 40 extending through the center of the spring 38. The barbed end 42 is split so that it can be compressed during the assembly of the system.

The shell 34 has a upper end 44 with a hole 46 through the center thereof, a cylindrical wall 48 and an open lower end 50. The open lower end 50 is designed to connect to the open upper end 26 of the cap 12. The hole 46 in the shell upper end 44 is sized so that the compressed barbed end 42 of the shaft 40 can be inserted therethrough but can not be readily withdrawn once inserted without forcibly compressing the shaft 40.

Figure 2:
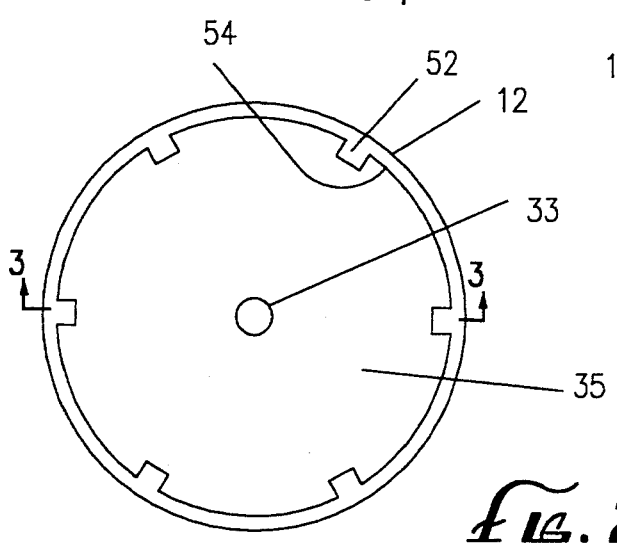
FIG. 2 is a top view of the cap portion of the fluid delivery system of FIG. 1.
Figure 3:
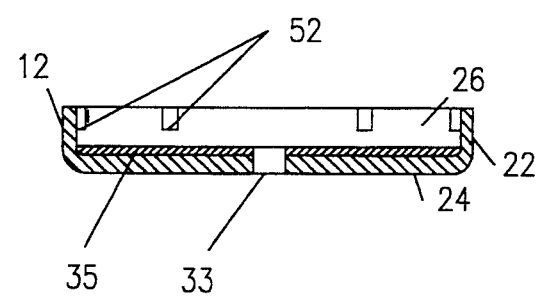
FIG. 3 is a cutaway side view of the cap portion of the fluid delivery system taken along line 3—3 of FIG. 1.

Various different means can be used to hold the cap 12 to the shell. FIGS. 1 through 3 show inwardly extending tabs 52 on the inner surface 54 of the cap 12. The tabs 52 are sized to fit through grooves 56 on the lower end 50 of the shell 34 and lock into a matching recess 58 on the upper ledge 60 of the shell bottom end 50 when the shell 34 is connected to the cap 12. Along the bottom of the inner surface of the cap is a soft liner 35 which is compressibly deformed by the connection of the cap to the shell, thus, aiding in holding the parts together. Alternate connecting means include threaded surfaces, latching mechanisms, rivets or screws.

Enclosed within the shell 34 is piston 18 which has a pressure surface 62 perpendicular to the shell wall 48. Extending laterally from the piston 18 edge are several fingers 64 which ride in vertical slots 66 in the inner wall of the shell 34. Guided by the fingers 64 and the slots 66, the piston 18 is free to move up and down within the shell 34. Extending upward from the piston 18 is a piston shaft 40 designed to releasably latch outside the shell and interlock with the top of the shell. In the embodiment, shown the latch release is a knob 36 which has release means, such as a cammed surface 68, on its inner surface designed to mate with the top of the piston shaft 40. The knob protects the top of the shaft and the cammed surface compresses the barbed shaft 42 after assembly when release by the operator is desired. Release is accomplished by rotating the knob 36.

Located within the shell 34 between the shell upper end 44 and the piston 18 is the spring 38. The spring 38 is designed to push the piston 18 toward the shell lower end 50 with a constant force. This is accomplished by various different mechanisms. For example, the spring can be cut from a single piece of spring steel or molded from a stiff plastic material with the width of each turn of the spring increasing along the spring length. A second alternative is a spring with a thickness varying along its width. Thirdly, the spring can be formed from two different materials laminated together with the ratio of the materials varying along the spring length. In a like manner, the same variations in spring design can be used to produce a driving force which varies in a preset manner.

FIGS. 11 through 13 show various different spring designs which may be used in the fluid delivery system 10 of the invention. FIGS. 11a and 11b show side and top views of a coil spring 70. In this instance, the cross section of the winding has a greater height than width, the height being selected to obtained the desired force curve as the spring expands. FIGS. 12a and 12b show side and top views of a dome spring 72 which has a base portion 74 and a top portion 76 connected by integral struts 78. As the dome spring 72 is compressed the base and/or the top can flatten and the struts 78 bow. Again, the cross section of the struts 78, base 74 and cap 76 can be varied to control the force of the spring as it expands.

FIG. 13 shows a spring 80 based on the negator principle. A spring wire 80 is wound around left and right wheels 84, 86. The spring wire 80 is tensioned by moving the piston 88 upwards against the wire 82.

Figure 14:
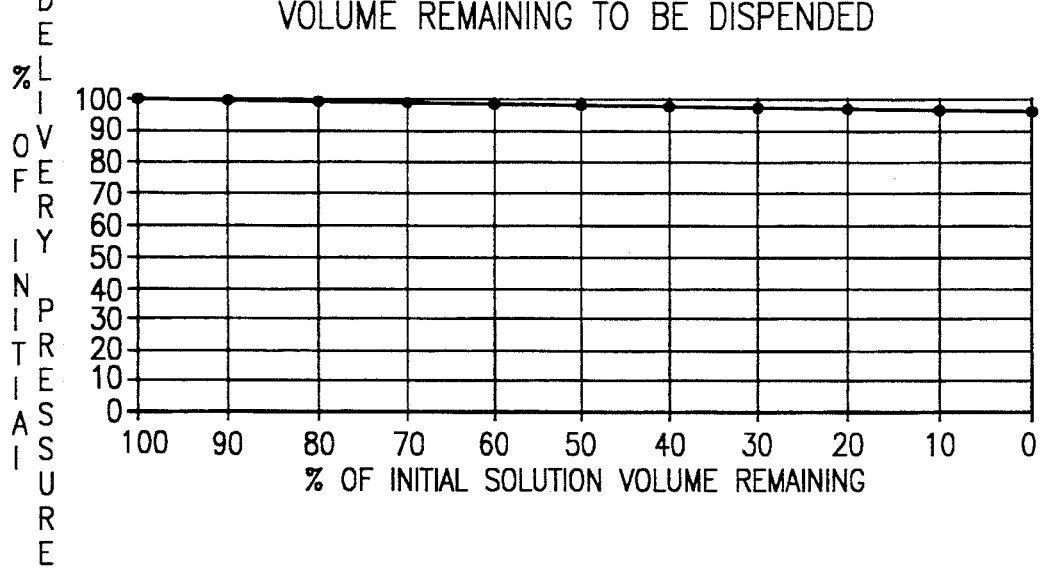
FIG. 14 shows a spring force curve for the constant rate springs shown in FIGS. 11 through 13.

The above-described springs can be formed from various materials or combinations of materials. While spring steel is the preferred materials various other high modulus metals, plastics or a combination of materials may be used. Also, a combination of different grades of a material, where the different grades have different moduli may be used. FIG. 14 shows the spring force (delivery pressure) as a function of spring extension (% volume remaining) for the constant force springs described above.

Figure 8:
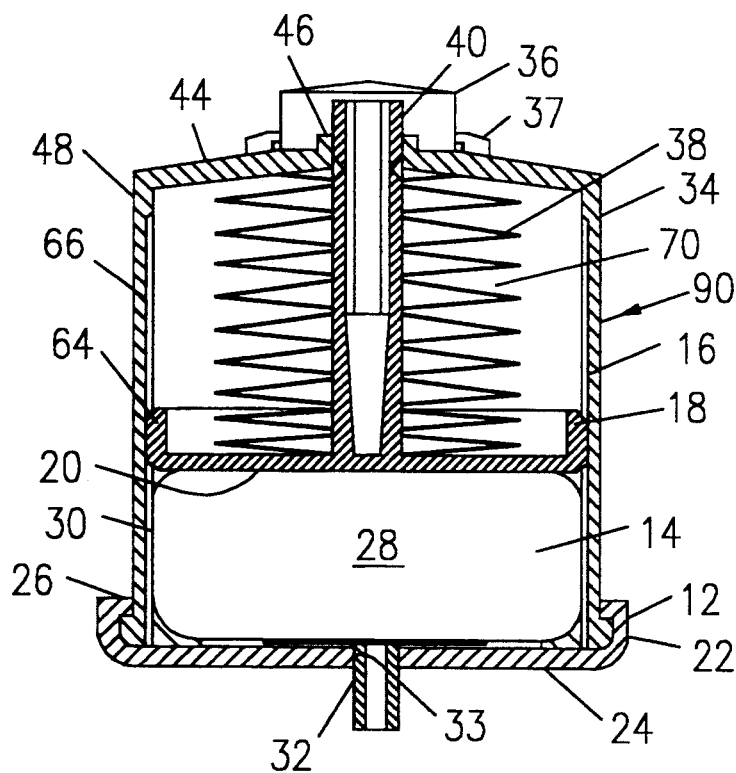
FIG. 8 is a cut away side view of a second embodiment of the fluid delivery system of FIG. 1.
Figure 9:
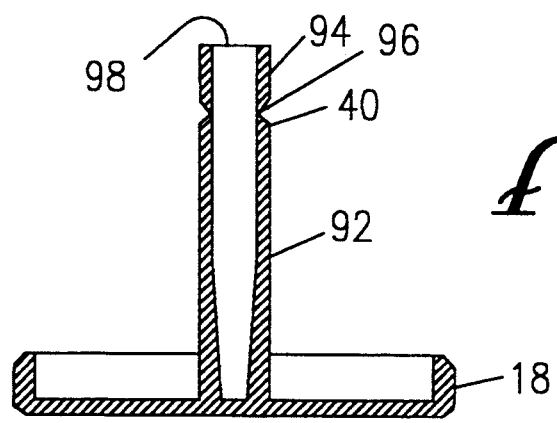
FIG. 9 is a side view of the piston used in the fluid delivery system of FIG. 8.

FIGS. 8 and 9 are directed to a second embodiment, preferably for applications where the fluid delivery system 90 is not to be refilled. The piston 18 has a weakened portion which is designed to allow the piston 18 and lower shaft 92 to be separated from the upper shaft 94 which is connected to the knob 36. As best shown in FIG. 9, the shaft has a narrowed portion 96 and a hollow center 98 which results in a thin wall portion which is readily broken by applying a twisting force to the upper shaft portion 92 by rotating the knob 36. The fingers 64 riding in the slots 66 prevent the lower shaft 92 and the piston 18 from rotating when the knob 36 is turned.

FIGS. 5 and 7 show a tubing set 100 attached to the tubing connector 32 on the bladder 14. Different tubing set 100 configurations can be used to match the specific delivery requirements of the physician, patient and the fluid being delivered. The particular arrangement shown includes a spike 102 connected to the tubing connector 32, a filter system 104 for trapping particulate matter and to remove gas bubbles, a clamp or a valve 106 and an outlet for attachment to a tube or catheter which, in turn, is emplaced in the patient. In a further embodiment, the outlet 108 in the tubing set 100 can also contain one or more metering orifices which, in conjunction with the known spring force, further controls the flow rate.

Shown on FIG. 1 is an accessory holder 110 which snaps onto the bottom of the cap 12 to hold the tubing set 100 and other accessories which are used with the fluid delivery system.

To assemble the embodiment of FIGS. 1 through 7 the piston 18 is forced upward into the shell 34 so that the barbed end 42 of the piston shaft 40 is inserted through the hole 46 in the upper end 44 of the shell 34 and the barbed end 42 is allowed to expand. Forcing the piston 18 into the shell 34 compresses the spring 38 and thus loads the drive mechanism 16. As the barbed end 42 exits through the hole 46 in the upper end 44 of the shell 34 the barbs are inserted into the cammed inner surface 68 of the knob 36 and the knob 36 is twisted, catching the barbs within the cam. The filled bladder 14 is placed in the cap 12 and the cap 12 carrying the bladder 14 is connected to the shell 34 by placing the tabs 52 through the grooves 56 in the shell ledge 60 and pressing and twisting the cap 12 to place the tab 52 in the recess 58 on the shell ledge 80. The desired tubing set 100 is then attached to the tubing connector 32. To use the fluid delivery system 10 the knob 36 is turned compressing the barbed upper end 42 which allows the compressed barbs to pass through the hole 46 in the upper end 44 of the shell 34 driven by the expanding spring 38. The system 10 can be reused by removing the cap 12, replacing the empty bladder 14 with a full bladder 14 and reassembling the system 10.

The embodiment of FIGS. 8 and 9 is assembled in a similar manner except that the cap 12 snaps onto the shell 34 so that once assembled it is not readily disassembled. Also the piston shaft 40 is frangible so that untwisting the knob 36 after assembly does not release the shaft 40 but instead causes the shaft 40 to break at the narrowed portion 96, thus rendering the system non-reusable without replacing the piston 18 and shaft 40 assembly.

Although the present invention has been described in considerable detail with reference to certain preferred versions and uses thereof, other versions and uses are possible. For example, various different means can be used to assemble the device or hold the components together, various different sizes and shapes of bladders can be used, and various different spring designs can be utilized to deliver a continuous constant drive force. Alternately, the spring can be designed to give several predetermined but different force cycles. For example, it may be desirable to deliver a bolus of fluid followed by a one or more periods of constant rate or fixed decreasing delivery rates. This can be accomplished by varying the spring design. Therefore, the spirit and scope of the appended claims should not be limited to the description of the preferred versions contained herein.

What is claimed is:

1. A fluid delivery system comprising:
   a drive mechanism connected to a cap with a hollow compressible bladder which can be filled with a material to be dispensed, the bladder being located between the drive mechanism and the cap,
   the hollow compressible bladder having access means for connecting an internal space within the bladder to a flow tube, and
   the cap holding the compressible bladder with the access means accessible through an opening in the cap, the cap having an open end and a closed end with an upper surface of the bladder being exposed to view through the open end of the cap,
   the drive mechanism comprising:
   a shell having a top and a cylindrical wall, the wall having a length, a diameter and an upper end and a lower end, the top of the shell being located on the upper end of the wall, the lower end of the wall having first securing means thereon cooperating with second securing means on the cap to attach the drive mechanism to the open end of the cap to form an assembled fluid delivery system having a space enclosing the bladder within the shell and the cap when the shell is attached to the cap,
   a piston located within the shell, said piston being moveable within the assembled fluid delivery system from a loaded position to an unloaded position, the piston being located between the upper end of the wall and the lower end of the wall in the loaded position and the piston in the unloaded position being located further from the upper end of the wall and closer to the lower end of the wall than in the loaded position, the piston being in contact with the upper surface of the bladder throughout a movement of the piston from the loaded position to the unloaded position,
   a pressure delivery means positioned between the piston and the top of the shell, the pressure delivery means being a spring formed from a spirally wound wire having a fixed length, the spring being capable of expanding from a compressed configuration to an expanded configuration and exerting a substantially constant preset force against the piston when expanding from the compressed configuration to the expanded configuration,
   a shaft extending from the piston and through the pressure delivery means, an upper end of the shaft extending through and held in an opening in a central portion of the top of the shell when the piston is in the loaded position, and
   a movable knob positioned over the opening in the central portion of the top of the shell, said knob mateable to the upper end of the shaft to prevent the piston from accidentally being released from the loaded position and rotatable to release the shaft such that rotating of the knob releases the shaft, allowing the pressure delivery means to push the piston towards the cap, compressing the bladder and forcing material contained within the bladder to be expelled through the access means in the bladder.

2. The fluid delivery system of claim 1 wherein the hollow bladder is cylindrical in shape and has a diameter and height chosen to enclose a known volume of material.

3. The fluid delivery system of claim 2 wherein the access means to the bladder is a tubing connector extending through an opening in the closed end of the cap.

4. The fluid delivery system of claim 1 further including a tubing set attached to the access means on the bladder.

5. The fluid delivery system of claim 4 wherein the tubing set includes flow restriction means.

6. The fluid delivery system of claim 1 wherein the upper end of the shaft has a barbed end, and the barbed end is positioned in the knob such that rotation of the knob disconnects the barbed end from the knob allowing the material in the bladder to be expelled in a controlled manner.

7. The fluid delivery system of claim 1 wherein the shaft has a weakened portion between the piston and the upper end of the shaft, the upper end of the shaft being attached to the knob so that rotation of the knob causes the shaft to break at the weakened portion.

8. The fluid delivery system of claim 1 wherein the the preset force of the spring results from the wire having different dimensions at different locations along the length of the wire.

9. The fluid delivery system of claim 1 wherein the preset force of the spring results from forming the spring from at least two materials having different elastic moduli.

10. A fluid delivery system comprising:
    a hollow compressible bladder for receiving a fluid to be delivered and a drive mechanism and cap assembly designed to enclose the bladder, the drive mechanism including pressure means for dispensing fluid contained in the bladder at a preset constant rate, the drive mechanism comprising a cup shaped shell having a cylindrical wall with a lower open end on a first end of the cylindrical wall and a closed upper end spaced from the lower open end, and a piston having a circular cross-section, the piston being located within the cylindrical wall, the piston being free to move from a first position adjacent to the closed upper end but spaced form the open lower end to a second position wherein the piston is spaced further away from the closed upper end but closer to the open lower end than in the first position, the pressure means is an expandable spring which generates a preset force against the piston, the preset force resulting from forming the spring from at least two materials having different elastic moduli, the pressure means being located in a space between the closed upper end of the shell and the piston, the cap being attached to the lower open end of the wall in a manner so that it can be removed and reattached, such that a bladder holding space is formed between the cap and the piston, the hollow compressible bladder being located in the bladder holding space, the bladder being in contact with and positioned between both the cap having a hole therein, the hole allowing access to an access port in a wall of the bladder, the drive mechanism further having a shaft attached at one end to, and extending perpendicular from, the piston, a portion of the shaft extending through a hole in the closed upper end of the shell and releasing means attached to the portion of the shaft extending through the hole in the closed end of the shell, the releasing means functioning to prevent the pressure means from exerting pressure on the piston until the shaft is disconnected from the releasing means.

11. The fluid delivery system of claim 10 wherein the pressure means is an expandable spring designed to exert a preset and constant pressure against the piston.

12. The fluid delivery system of claim 10 wherein the hollow compressible bladder is removable from the fluid delivery system, the bladder being sized to receive a known quantity of fluid prior to placement in the bladder space.

13. The fluid delivery system of claim 10 further including an accessory holder attached to an outer surface of the cap, the accessory holder enclosing a tubing set in a space between the cap and the accessory holder.

14. The fluid delivery system of claim 10 wherein the portion of the shaft extending through the shell has a barbed end, the barbed end is held in the releasing means such that rotation of the releasing means releases the barbed end allowing the fluid in the bladder to be expelled in a controlled manner.

15. The fluid delivery system comprising:

a drive mechanism connected to a cap with a hollow compressible bladder which can be filled with a material to be dispensed, the bladder being located between the drive mechanism and the cap, the hollow compressible bladder having access means for connecting an integral space within the bladder to a flow tube, and the cap holding the compressible bladder with the access means accessible through an opening in the cap, the cap having an open end and a closed end with an upper surface of the bladder being exposed to view through the open end of the cap, the drive mechanism comprising:

a shell having a top and a cylindrical wall, the wall having a length, a diameter and an upper end and a lower end, the top of the shell being located on the upper end of the wall, the lower end of the wall having first securing means thereon cooperating with second securing means on the cap to attach the drive mechanism to the open end of the cap to form an assembled fluid delivery system having a space enclosing the bladder within the shell and the cap when the shell is attached to the cap, a piston located within the shell, said piston being moveable within the assembled fluid delivery system from a loaded position to an unloaded position, the piston being located between the upper end of the wall and the lower end of the wall in the loaded position and the piston in the unloaded position being located further from the upper end of the wall and closer to the lower end of the wall than in the loaded position, the piston being in contact with the upper surface of the bladder throughout a movement of the piston from the loaded position to the unloaded position, a pressure delivery means delivering a preset force against the piston positioned between the piston and the top of the shell, the preset force being a combination of at least a first and a second preset force level, the first preset force level being generated upon rotating of the knob to release the shaft and the second preset force level being generated during the compression of the bladder, a shaft extending from the piston and through the pressure delivery means, an upper end of the shaft extending through and held in an opening in a central portion of the top of the shell when the piston is in the loaded position, and a movable knob positioned over the opening in the central portion of the top of the shell, said knob mateable to the upper end of the shaft to prevent the piston from accidentally being released from the loaded position and rotatable to release the shaft such that rotating of the knob releases the shaft, allowing the pressure delivery means to push the piston towards the cap, compressing the bladder and forcing material contained within the bladder to be expelled through the access means in the bladder.

16. A fluid delivery system comprising:

a hollow compressible bladder for receiving a fluid to be delivered and a drive mechanism and cap assembly designed to enclose the bladder, the drive mechanism including pressure means for dispensing fluid contained in the bladder at a preset constant rate, the drive mechanism comprising a cup shaped shell having a cylindrical wall with a lower open end on a first end of the cylindrical wall and a closed upper end spaced from the lower open end, and a piston having a cylindrical wall, the piston being free to move from a first position adjacent to the closed upper end but spaced form the open lower end to a second position wherein the piston is spaced further away from the closed upper end but closer to the open lower end than in the first position, the pressure means being located in a space between the closed upper end of the shell and the piston and exerting a substantially constant force against the piston, the cap being attached to the lower open end of the wall in a manner so that it can be removed and reattached, such that a bladder holding space is formed between the cap and the piston, the hollow compressible bladder being located in the bladder holding space, the bladder being in contact with and positioned between both the cap and the piston when the bladder contains the fluid, the cap having a hole therein, the hole allowing access to an access port in a wall of the bladder, the drive mechanism further having a shaft attached at one end to, and extending perpendicular from, the piston, a portion of the shaft extending through a hole in the closed upper end of the shell and releasing means attached to the portion of the shaft extending through the hole in the closed end of the shell, the releasing means functioning to prevent the pressure means from exerting pressure on the piston until the shaft is disconnected by the releasing means.

17. The fluid delivery system of claim 16 wherein the preset force is a combination of at least a first and a second preset force level, the first preset force level being generated upon disconnecting the shaft from the releasing means and the second preset force level being generated as the piston moves from the first position to the second position.

* * * * *